United States Patent
Grendze et al.

(10) Patent No.: US 10,414,723 B2
(45) Date of Patent: Sep. 17, 2019

(54) PROCESSES FOR CONVERTING CARBOXAMIDES TO THIOCARBOXAMIDES

(71) Applicant: Vertellus Holdings LLC, Indianapolis, IN (US)

(72) Inventors: Martin P. Grendze, Indianapolis, IN (US); Ramiah Murugan, Indianapolis, IN (US)

(73) Assignee: VERTELLUS HOLDINGS LLC, Indianapolis, IN (US)

( * ) Notice: Subject to any disclaimer, the term of this patent is extended or adjusted under 35 U.S.C. 154(b) by 0 days.

(21) Appl. No.: 15/572,451

(22) PCT Filed: May 6, 2016

(86) PCT No.: PCT/US2016/031177
§ 371 (c)(1),
(2) Date: Nov. 7, 2017

(87) PCT Pub. No.: WO2016/182900
PCT Pub. Date: Nov. 17, 2016

(65) Prior Publication Data
US 2018/0118675 A1    May 3, 2018

Related U.S. Application Data

(60) Provisional application No. 62/158,909, filed on May 8, 2015.

(51) Int. Cl.
| | | |
|---|---|---|
| *C07C 327/46* | (2006.01) | |
| *C07D 211/60* | (2006.01) | |
| *C07B 45/00* | (2006.01) | |
| *C07C 327/42* | (2006.01) | |
| *C07C 327/44* | (2006.01) | |
| *C07F 9/165* | (2006.01) | |

(52) U.S. Cl.
CPC ........... *C07C 327/46* (2013.01); *C07B 45/00* (2013.01); *C07C 327/42* (2013.01); *C07C 327/44* (2013.01); *C07D 211/60* (2013.01); *C07F 9/165* (2013.01)

(58) Field of Classification Search
None
See application file for complete search history.

(56) References Cited

U.S. PATENT DOCUMENTS

| 4,049,755 A * | 9/1977 | Bianchi ................. C07F 9/1651 |
| | | 558/112 |
| 2010/0144817 A1 | 6/2010 | Desbordes |
| 2010/0234395 A1 | 9/2010 | Sugawara et al. |
| 2012/0088748 A1 | 4/2012 | Ishichi et al. |

FOREIGN PATENT DOCUMENTS

| WO | WO-2004041815 A1 * | 5/2004 | ........... C07D 417/12 |
| WO | 2005095425 A1 | 10/2005 | |
| WO | 2011072207 A1 | 6/2011 | |

OTHER PUBLICATIONS

Borthakur ("New Direct Synthesis of Thioamides from Carboxylic Acids" Tetrahedron Letters, vol. 36, No. 37, 1995, p. 6745-6746) (Year: 1995).*
Wang ("Molecular Thioamide<--> Iminothiolate Switches for Sulfur Mustards" Inorganic Chemistry, 2012, 51, p. 760-762, including SI pp. S1-S17) (Year: 2012).*
Sigma Aldrich product page for the Lawesson reagent, downloaded from https://www.sigmaaldrich.com/catalog/product/aldrich/227439?lang=en&region=US on Sep. 12, 2018. (Year: 2018).*
Sigma Aldrich product page for Toluene, downloaded from https://www.signnaaldrich.com/chemistry/solvents/toluene-center.html on Feb. 9, 2019 (Year: 2019).*
Kaboudin et al. 'Ammonium Phosphorodithioate: A Mild, Easily Handled, Efficient, and Air-Stable Reagent for the Conversion of Amides into Thioamides', Synlett 2011, vol. 19, pp. 2807-2810.
Kaboudin et al. 'A simple and novel method for the direct conversion of carboxylic acids into thioamides', RSC Adv., 2013, vol. 3, pp. 6435-6441.
Perregaard et al., "Studies on Organophosphorus Compunds XVI—On O, O-Dialkyl Dithiophosphoric Acids and N, N, N',N'-Tetramethylthiophosphoric Diamide as Thiation Agents: Conversion of Carboxamides into Thiocarboxamides, Alkyl Dithiocarboxylates, or Nitriles," Bull. Soc. Chim. Belg. vol. 86, No. 4, 1977.
International Search Report and Written Opinion Prepared for PCT/US16/31177, dated Aug. 12, 2016, 8 pages.

* cited by examiner

*Primary Examiner* — Amy C Bonaparte
(74) *Attorney, Agent, or Firm* — Barnes & Thornburg, LLP

(57) ABSTRACT

Process for converting a carboxamide to a thiocarboxamide includes reacting (a) a substrate that comprises a heteroatom-containing moiety and a carboxamide moiety with (b) a dialkyl dithiophosphate and/or a salt thereof. The heteroatom-containing moiety includes a heteroatom selected from the group consisting of N, O, and S. Processes for preparing piperidine-4-thiocarboxamide are described.

10 Claims, No Drawings

PROCESSES FOR CONVERTING CARBOXAMIDES TO THIOCARBOXAMIDES

CROSS REFERENCE TO RELATED APPLICATIONS

This application is a national stage entry made under 35 U.S.C. § 371(b) of PCT International Application No. PCT/US2016/031177, filed May 6, 2016, which claims priority under 35 U.S.C. § 119(e) to U.S. Provisional Application Ser. No. 62/158,909, filed May 8, 2015, which is incorporated herein by reference in its entirety.

TECHNICAL FIELD

The present teachings relate generally to synthetic organic methodology and, more particularly, to thionation reactions.

BACKGROUND

The conversion of a carboxamide substrate to a thiocarboxamide product using conventional thionating agents (e.g., $P_4S_{10}$, Lawesson's Reagent) may be hindered by the presence of heteroatoms in the carboxamide substrate.

By way of example, in the presence of a conventional thionating agent, a heterocyclic carboxamide substrate containing one or more nitrogen heteroatoms (e.g., a carboxamide-substituted piperdine and/or the like) may undergo dehydrogenation to form a pyridinyl material rather than the desired thionated product. As a result, circuitous synthetic pathways that involve the preparation of synthetic intermediates (e.g., cyano compounds), protection-deprotection sequences, and/or the like may be required to effect the desired conversion of a carboxamide substrate to a thiocarboxamide product.

SUMMARY

The scope of the present invention is defined solely by the appended claims, and is not affected to any degree by the statements within this summary.

By way of introduction, a first process for converting a carboxamide to a thiocarboxamide in accordance with the present teachings includes reacting (a) a substrate that comprises a heteroatom-containing moiety and a carboxamide moiety with (b) a dialkyl dithiophosphate and/or a salt thereof. The heteroatom-containing moiety includes a heteroatom selected from the group consisting of N, O, and S.

A second process for converting a carboxamide to a thiocarboxamide in accordance with the present teachings includes:

reacting a substrate of formula VII

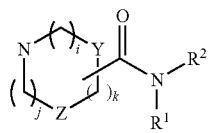

VII with a dialkyl dithiophosphate and/or a salt thereof;
wherein Y and Z are independently selected from the group consisting of N, O, S, a bond, and an optionally substituted carbon atom;

wherein i is an integer value ranging from 1 through 20;
wherein j and k are integer values independently ranging from 0 through 20; and
wherein $R^1$ and $R^2$ are independently selected from the group consisting of hydrogen, alkyl, alkenyl, aryl, and heteroaryl;
with a proviso that when each of Y and Z is a bond, then at least one of j and k is non-zero.

A first process for preparing piperidine-4-thiocarboxamide in accordance with the present teachings includes directly converting piperidine-4-carboxamide to piperidine-4-thiocarboxamide without traversing a 4-cyanopiperdine intermediate.

A second process for preparing piperidine-4-thiocarboxamide in accordance with the present teachings includes reacting piperidine-4-carboxamide with diethyl dithiophosphate and/or a salt thereof in an aromatic solvent.

Several illustrative embodiments of the present teachings may be described by the following enumerated clauses:

1. A process for converting a carboxamide to a thiocarboxamide, the process comprising:

reacting (a) a substrate that comprises a heteroatom-containing moiety and a carboxamide moiety with (b) a dialkyl dithiophosphate and/or a salt thereof;

wherein the heteroatom-containing moiety comprises a heteroatom selected from the group consisting of N, O, and S.

2. The process of the preceding clause wherein the substrate has a structure of formula I:

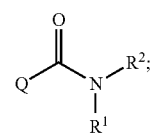

I wherein Q is heterocyclic; and
wherein $R^1$ and $R^2$ are independently selected from the group consisting of hydrogen, alkyl, alkenyl, aryl, and heteroaryl.

3. The process of any one of the preceding clauses wherein Q has a structure of formula II:

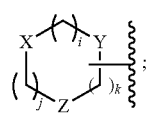

II wherein X is a heteroatom;
wherein Y and Z are independently selected from the group consisting of a heteroatom, a bond, and an optionally substituted carbon atom;
wherein i is an integer value ranging from 1 through 20; and
wherein j and k are integer values independently ranging from 0 through 20;
with a proviso that when each of Y and Z is a bond, then at least one of j and k is non-zero.

4. The process of any one of the preceding clauses wherein the substrate has a structure of formula III:

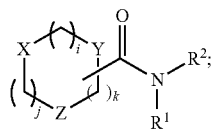

wherein X is a heteroatom;

wherein Y and Z are independently selected from the group consisting of a heteroatom, a bond, and an optionally substituted carbon atom;

wherein i is an integer value ranging from 1 through 20;

wherein j and k are integer values independently ranging from 0 through 20; and wherein $R^1$ and $R^2$ are independently selected from the group consisting of hydrogen, alkyl, alkenyl, aryl, and heteroaryl;

with a proviso that when each of Y and Z is a bond, then at least one of j and k is non-zero.

5. The process of any one of the preceding clauses wherein the heteroatom-containing moiety comprises a nitrogen atom.

6. The process of any one of the preceding clauses wherein the heteroatom-containing moiety comprises a heterocyclic moiety selected from the group consisting of aziridine, azirine, diazirine, oxaziridine, azetidine, azete, diazetidine, pyrrolidine, pyrrole, imidazolidine, imidazole, pyrazolidine, pyrazole, oxazolidine, oxazole, isoxazolidine, isoxazole, thiazolidine, thiazole, isothiazolidine, isothiazole, triazoles, furazan, oxadiazole, thiadiazole, dithiazole, tetrazole, piperidine, pyridine, piperazine, diazines, morpholine, oxazine, thiomorpholine, thiazine, triazine, tetrazine, azepane, azepine, homopiperazine, diazepine, thiazepine, azocane, azocine, tetrahydropyran, and combinations thereof.

7. The process of any one of the preceding clauses wherein the substrate has a structure of formula IV:

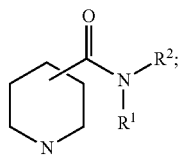

wherein $R^1$ and $R^2$ are independently selected from the group consisting of hydrogen, alkyl, alkenyl, aryl, and heteroaryl.

8. The process of any one of the preceding clauses wherein the substrate has a structure of formula V:

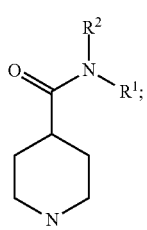

wherein $R^1$ and $R^2$ are independently selected from the group consisting of hydrogen, alkyl, alkenyl, aryl, and heteroaryl.

9. The process of any one of the preceding clauses wherein $R^1$ and $R^2$ are hydrogen.

10. The process of any one of the preceding clauses wherein the dialkyl dithiophosphate is selected from the group consisting of dimethyl dithiophosphate, diethyl dithiophosphate, di-(2-methoxyethyl) dithiophosphate, di-n-propyl dithiophosphate, di-iso-propyl dithiophosphate, di-n-butyl dithiophosphate, di-iso-butyl dithiophosphate, di-sec-butyl dithiophosphate, di-tent-butyl dithiophosphate, di-n-octyl dithiophosphate, and combinations thereof.

11. The process of any one of the preceding clauses wherein the dialkyl dithiophosphate comprises diethyl dithiophosphate.

12. The process of any one of the preceding clauses wherein the dialkyl dithiophosphate comprises diethyl dithiophosphate.

13. The process of any one of the preceding clauses wherein the substrate comprises a plurality of carboxamide moieties, and wherein the process further comprises converting more than one of the plurality of carboxamide moieties to a thiocarboxamide.

14. The process of any one of the preceding clauses further comprising generating the dialkyl dithiophosphate in situ by reacting $P_4S_{10}$ and an alkyl alcohol.

15. The process of any one of the preceding clauses wherein the substrate has a structure of formula VI:

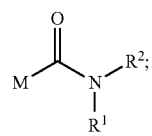

wherein M is alkyl, alkenyl, alkynyl, or aryl and a carbon atom of M is attached to a heteroatom-containing substituent, or wherein M is heteroaryl; and wherein $R^1$ and $R^2$ are independently selected from the group consisting of hydrogen, alkyl, alkenyl, aryl, and heteroaryl.

16. A process for preparing piperidine-4-thiocarboxamide comprising:

directly converting piperidine-4-carboxamide to piperidine-4-thiocarboxamide without traversing a 4-cyanopiperdine intermediate.

17. A process for converting a carboxamide to a thiocarboxamide, the process comprising:

reacting a substrate of formula VII:

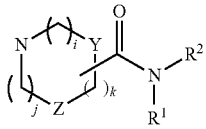

with a dialkyl dithiophosphate and/or a salt thereof;

wherein Y and Z are independently selected from the group consisting of N, O, S, a bond, and an optionally substituted carbon atom;

wherein i is an integer value ranging from 1 through 20;
wherein j and k are integer values independently ranging from 0 through 20; and
wherein $R^1$ and $R^2$ are independently selected from the group consisting of hydrogen, alkyl, alkenyl, aryl, and heteroaryl;
with a proviso that when each of Y and Z is a bond, then at least one of j and k is non-zero.

18. The process of the preceding clause wherein Y and Z are independently selected from the group consisting of N and C.

19. The process of any one of the preceding clauses wherein the dialkyl dithiophosphate comprises diethyl dithiophosphate.

20. A process for preparing piperidine-4-thiocarboxamide comprising:
reacting piperidine-4-carboxamide with diethyl dithiophosphate and/or a salt thereof in an aromatic solvent.

DETAILED DESCRIPTION

Processes for the thionation of carboxamides have been discovered and are described herein. As further described below, dialkyl dithiophosphates are used as thionating agents. The dialkyl dithiophosphates may be pre-formed (e.g., such as commercially available dialkyl dithiophosphates) or generated in situ (e.g., from $P_4S_{10}$ and a stoichiometric amount of alcohol). Furthermore, processes in accordance with the present teachings may be used to thionate substrates that contain one or a plurality of heteroatoms (i.e., heteroatoms in addition to the nitrogen and oxygen heteroatoms that constitute the carboxamide moiety itself). Such heteroatoms may interfere with conventional thionation agents (e.g., $P_4S_{10}$, Lawesson's Reagent, etc.).

Throughout this description and in the appended claims, the following definitions are to be understood:

The term "heteroatom" refers to any atom other than carbon and hydrogen. Representative examples of heteroatoms in accordance with the present teachings include but are not limited to nitrogen, oxygen, sulfur, and the like.

The term "alkyl" refers to a substituted or unsubstituted, straight, branched or cyclic hydrocarbon chain containing, in some embodiments, from 1 to 20 carbon atoms. Representative examples of unsubstituted alkyl groups in accordance with the present teachings include but are not limited to methyl, ethyl, propyl, iso-propyl, cyclopropyl, butyl, iso-butyl, tert-butyl, sec-butyl, cyclobutyl, pentyl, cyclopentyl, hexyl, cyclohexyl, and the like.

The term "alkenyl" refers to a substituted or unsubstituted, straight, branched or cyclic, unsaturated hydrocarbon chain that contains at least one double bond and, in some embodiments, from 2 to 20 carbon atoms. Representative unsubstituted alkenyl groups in accordance with the present teachings include but are not limited to ethenyl or vinyl (—CH═$CH_2$), 1-propenyl, 2-propenyl or allyl (—$CH_2$—CH═$CH_2$), 1,3-butadienyl (—CH═CHCH═$CH_2$), 1-butenyl (—CH═CH$CH_2$$CH_3$), hexenyl, pentenyl, 1, 3, 5-hexatrienyl, and the like. In some embodiments, cycloalkenyl groups have from five to eight carbon atoms and at least one double bond. Representative cycloalkenyl groups in accordance with the present teachings include but are not limited to cyclohexadienyl, cyclohexenyl, cyclopentenyl, cycloheptenyl, cyclooctenyl, cyclohexadienyl, cycloheptadienyl, cyclooctatrienyl, and the like.

The term "alkynyl" refers to a substituted or unsubstituted, straight, branched or cyclic unsaturated hydrocarbon chain containing at least one triple bond and, in some embodiments, from 2 to 20 carbon atoms.

The term "aryl" refers to a substituted or unsubstituted mono-, bi-, or poly-cyclic aromatic ring system of 4-20 carbon atoms. Representative aryl groups in accordance with the present teachings include but are not limited to benzene, substituted benzene (e.g., toluene, xylenes, styrene), naphthalene, anthracene, biphenyl, and the like.

The term "amino" refers to an unsubstituted or substituted amino (—$NH_2$) group. The amine may be primary (—$NH_2$), secondary (—$NHR^a$) or tertiary (—$NR^aR^b$, wherein $R^a$ and $R^b$ are the same or different). Representative substituted amino groups in accordance with the present teachings include but are not limited to methylamino, dimethylamino, ethylamino, diethylamino, 2-propylamino, 1-propylamino, di(n-propyl)amino, di(iso-propyl)amino, methyl-n-propylamino, tert-butylamino, and the like.

The term "heterocyclic" refers to a saturated, partially unsaturated, or aromatic ring system containing from 3 to 20 carbon atoms (in some embodiments, 4 to 8 carbon atoms) and at least one heteroatom (in some embodiments 1 to 3 heteroatoms). The ring may optionally be substituted with one or more substituents. Moreover, the ring may be mono-, bi- or polycyclic. Representative heteroatoms for inclusion in the ring include but are not limited to nitrogen, oxygen, and sulfur. As used herein, the term "heterocyclic" subsumes the term "heteroaryl." Representative heterocyclic groups in accordance with the present teachings include but are not limited to aziridine, azirine, oxirane, oxirene, thiirane, thiirene, diazirine, oxaziridine, dioxirane, azetidine, azete, oxetane, oxete, thietane, thiete, diazetidine, dioxetane, dioxete, dithietane, dithiete, pyrrolidine, tetrahydrofuran, thiolane, imidazolidine, pyrazolidene, oxazolidine, isooxazolidine, thiazolidine, isothiazolidene, dioxolane, dithiolane, furazan, oxadiazole, dithiazole, tetrazole, piperidine, oxane, pyran, thiane, thiopyran, piperazine, diazines, morpholine, oxazine, thiomorpholine, thiazine, dioxane, dioxine, dithiane, dithiine, trioxane, trithiane, tetrazine, azepane, azepine, oxepane, oxepine, thiepane, thiepine, homopiperazine, diazepine, thiazepine, azocane, azocine, acridine, benzathiazoline, benzimidazole, benzofuran, benzothiapene, benzthiazole, benzothiophenyl, carbazole, cinnoline, furan, imidazole, 1H-indazole, indole, isoindole, isoquinoline, isothiazole, oxazole, isoxazole, oxadiazoles (e.g., 1,2,3-oxadiazole), phenazine, phenothiazine, phenoxazine, phthalazine, pteridine, purine, pyrazine, pyrazole, pyridazine, pyridine, pyrimidine, pyrrole, quinazoline, quinoline, quinoxaline, thiazole, thiadiazoles (e.g., 1,3,4-thiadiazole), thiophene, triazine (e.g., 1,3,5-triazine), triazoles (e.g., 1,2,3-triazole), and the like.

The term "substituted" refers to the attachment of one or more substituents onto a backbone structure (e.g., an alkyl backbone, an alkenyl backbone, a heterocyclic backbone, etc.). Representative substituents for use in accordance with the present teachings include but are not limited to hydroxyl, amino (—$NH_2$, —$NHR^a$, —$NR^aR^b$), oxy (—O—), carbonyl (—CO—), thiol, alkyl, alkenyl, alkynyl, alkoxy, halo, nitrile, nitro, aryl and heterocyclyl groups. These substituents can optionally be further substituted with 1-3 substituents. Examples of substituted substituents include but are not limited to carboxamide, alkylmercapto, alkylsulphonyl, alkylamino, dialkylamino, carboxylate, alkoxycarbonyl, alkylaryl, aralkyl, alkylheterocyclyl, heterocyclylaryl, haloalkyl, and the like. The substituent should not substantially interfere chemically with the reaction of the invention (e.g., cross react with reactants, terminate the reaction or the like). Protecting groups may be used to protect functional substituents, as is well understood in the art (see: *Greene's Protective Groups in Organic Synthesis*, 5$^{th}$, Edition by Peter G. M. Wuts, John Wiley & Sons, Inc., New Jersey, 2014).

The term "alkoxy" refers to a substituted or unsubstituted —O-alkyl group. Representative unsubstituted alkoxy groups in accordance with the present teachings include but are not limited to methoxy, ethoxy, n-propoxy, iso-propoxy, n-butoxy, tert-butoxy, and the like.

It is to be understood that elements and features of the various representative embodiments described below may be combined in different ways to produce new embodiments that likewise fall within the scope of the present teachings.

By way of introduction, a first process for converting a carboxamide to a thiocarboxamide in accordance with the present teachings includes reacting (a) a substrate that comprises a heteroatom-containing moiety and a carboxamide moiety with (b) a dialkyl dithiophosphate and/or a salt thereof. In some embodiments, the heteroatom-containing moiety contains a heteroatom selected from the group consisting of N, O, and S.

In some embodiments, the substrate includes a plurality of carboxamide moieties (e.g., two or more), and the process further includes converting more than one (and, in some embodiments, each) of the plurality of carboxamide moieties to a thiocarboxamide.

All manner of carboxamide-containing substrates are contemplated for use in accordance with the present teachings—including but not limited to substrates that contain one or more heterocyclic rings. For example, in some embodiments, the substrate has a structure of formula I:

$$\text{Q} \overset{\text{O}}{\underset{\text{R}^1}{\overset{\|}{\text{C}}}} \text{N} - \text{R}^2;$$

I wherein Q is heterocyclic; and wherein $R^1$ and $R^2$ are each independently selected from the group consisting of hydrogen, alkyl, alkenyl, aryl, and heteroaryl.

In some embodiments, the substrate contains a heterocyclic, heteroatom-containing moiety having a structure of formula II:

II wherein X is a heteroatom; wherein Y and Z are independently selected from the group consisting of a heteroatom, a bond, and an optionally substituted carbon atom; wherein i is an integer value ranging from 1 through 20; and wherein j and k are integer values independently ranging from 0 through 20; with a proviso that when each of Y and Z is a bond, then at least one of j and k is non-zero.

In the structure of formula II, each of Y and Z is depicted as a divalent ring atom or a bond. Thus, when Y is a bond, then formula II becomes formula IIA:

IIA

Similarly, when Z is a bond, then formula II becomes formula IIB:

IIB

When each of Y and Z is a bond, then formula II becomes formula IIC:

IIC

When j is 0 in the structure of formula II, then X is attached to Z. When j is 0 and Z is a bond, then X is attached to the next atom in the chain. Similarly, when k is 0 in the structure of formula II, then Z is attached to Y. When k is 0 and Y is a bond, then Z is attached to the next atom in the chain.

In some embodiments, the substrate has a structure of formula III:

III wherein X is a heteroatom; wherein Y and Z are independently selected from the group consisting of a heteroatom, a bond, and an optionally substituted carbon atom; wherein i is an integer value ranging from 1 through 20; wherein j and k are integer values independently ranging from 0 through 20; and wherein $R^1$ and $R^2$ are independently selected from the group consisting of hydrogen, alkyl, alkenyl, aryl, and heteroaryl; with a proviso that when each of Y and Z is a bond, then at least one of j and k is non-zero.

In some embodiments, the heteroatom-containing moiety of the substrate includes one or a plurality of nitrogen atoms. In some embodiments, the one or the plurality of nitrogen atoms is present as an amine. In some embodiments, the heteroatom-containing moiety of the substrate includes an amine selected from the group consisting of a primary amine, a secondary amine, a tertiary amine, and combinations thereof.

In some embodiments, the heteroatom-containing moiety includes a heterocyclic moiety selected from the group consisting of aziridine, azirine, diazirine, oxaziridine, azetidine, azete, diazetidine, pyrrolidine, pyrrole, imidazolidine, imidazole, pyrazolidine, pyrazole, oxazolidine, oxazole, isoxazolidine, isoxazole, thiazolidine, thiazole, isothiazolidine, isothiazole, triazoles, furazan, oxadiazole, thiadiazole, dithiazole, tetrazole, piperidine, pyridine, piperazine, diazines, morpholine, oxazine, thiomorpholine, thiazine, triazine, tetrazine, azepane, azepine, homopiperazine, diazepine, thiazepine, azocane, azocine, and/or the like, and combinations thereof. In some embodiments, the heterocyclic moiety is selected from the group consisting of aziridine, azirine, azetidine, azete, pyrrolidine, pyrrole, piperdine, piperazine, pyridine, azepane, azepine, tetrahydropyran, and/or the like, and combinations thereof. In some embodiments, the heterocyclic moiety includes piperdine.

In some embodiments, the substrate has a structure of formula IV:

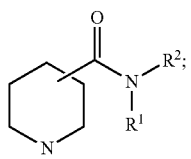

IV wherein $R^1$ and $R^2$ are independently selected from the group consisting of hydrogen, alkyl, alkenyl, aryl, and heteroaryl.

In some embodiments, the substrate has a structure of formula V:

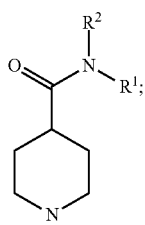

V wherein $R^1$ and $R^2$ are independently selected from the group consisting of hydrogen, alkyl, alkenyl, aryl, and heteroaryl. In some embodiments, each of $R^1$ and $R^2$ in formula V is hydrogen.

In some embodiments, the substrate has a structure of formula VI

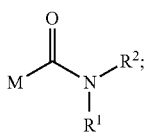

VI wherein M is alkyl, alkenyl, alkynyl, or aryl and a carbon atom of M is attached to a heteroatom-containing substituent, or wherein M is heteroaryl; and wherein $R^1$ and $R^2$ are independently selected from the group consisting of hydrogen, alkyl, alkenyl, aryl, and heteroaryl.

All manner of dialkyl dithiophosphates are contemplated for use in accordance with the present teachings. Dialkyl dithiophosphates in accordance with the present teachings may be purchased commercially, or prepared in situ (e.g., from $P_4S_{10}$ and a stoichiometric amount of alcohol) as shown in EQN. 1.

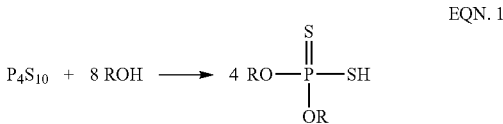

EQN. 1

While neither desiring to be bound by any particular theory nor intending to limit in any measure the scope of the appended claims or their equivalents, it is presently believed that the ease of product isolation may be affected by the nature of the alcohol on which the dialkyl dithiophosphate is based. In some embodiments, an excess of dialkyl dithiophosphate (e.g., 2.5 equivalents) is used to provide high conversion of carboxamide to thiocarboxamide.

In some embodiments, the dialkyl dithiophosphate is selected from the group consisting of dimethyl dithiophosphate, diethyl dithiophosphate, di-(2-methoxyethyl) dithiophosphate, di-n-propyl dithiophosphate, di-iso-propyl dithiophosphate, di-n-butyl dithiophosphate, di-iso-butyl dithiophosphate, di-sec-butyl dithiophosphate, di-tert-butyl dithiophosphate, di-n-octyl dithiophosphate, and/or the like, and combinations thereof. In some embodiments, the dialkyl dithiophosphate includes diethyl dithiophosphate.

In some embodiments, a process in accordance with the present teachings further includes generating the dialkyl dithiophosphate in situ by reacting $P_4S_{10}$ and an alkyl alcohol.

A second process for converting a carboxamide to a thiocarboxamide in accordance with the present teachings includes reacting a substrate of formula VII:

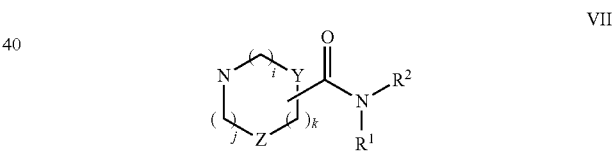

VII with a dialkyl dithiophosphate and/or a salt thereof, wherein (define all groups or state that they are as defined herein). In some embodiments, Y and Z are independently selected from the group consisting of N, O, S, a bond, and an optionally substituted carbon atom; i is an integer value ranging from 1 through 20; j and k are integer values independently ranging from 0 through 20; and $R^1$ and $R^2$ are independently selected from the group consisting of hydrogen, alkyl, alkenyl, aryl, and heteroaryl; with a proviso that when each of Y and Z is a bond, then at least one of j and k is non-zero. In some embodiments, Y and Z are independently selected from the group consisting of N and C. In some embodiments, the dialkyl dithiophosphate includes diethyl dithiophosphate.

Piperidine-4-thiocarboxamide (PTCA) (CAS No. 112401-09-9) 2 is a useful intermediate in the synthesis of various pharmaceutical and agricultural intermediates. Practical, safe, low-cost methods for the production of this material are thus of interest.

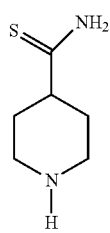

In some embodiments, as shown in EQN. 2, processes in accordance with the present teachings may be used for preparing piperidine-4-thiocarboxamide 2 directly from piperidine-4-carboxamide 1.

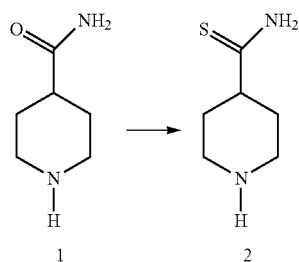

The piperidine-4-carboxamide 1 starting material may in turn be prepared from 4-cyanopyridine 3 via hydrolysis and hydrogenation, as shown in Scheme 1.

Scheme 1

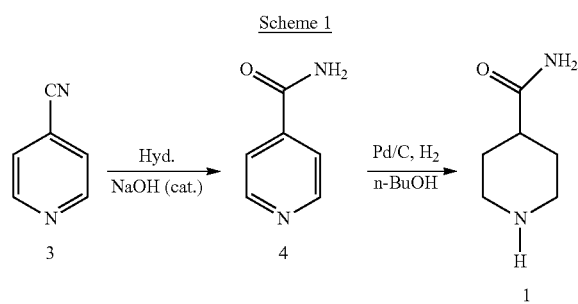 [SMILES: N#Cc1ccncc1 ; "n-BuOH" ; NC(=O)c1ccncc1 ; NC(=O)C1CCNCC1]

A first process for preparing piperidine-4-thiocarboxamide in accordance with the present teachings includes directly converting piperidine-4-carboxamide to piperidine-4-thiocarboxamide without traversing a 4-cyanopiperdine intermediate. In some embodiments, the direct conversion of piperidine-4-carboxamide to piperidine-4-thiocarboxamide has a yield of at least about 40%, in some embodiments at least about 45%, in some embodiments at least about 50%, in some embodiments at least about 55%, in some embodiments at least about 60%, in some embodiments at least about 65%, and in some embodiments greater than about 65%.

A second process for preparing piperidine-4-thiocarboxamide in accordance with the present teachings includes reacting piperidine-4-carboxamide with diethyl dithiophosphate and/or a salt thereof in an aromatic solvent.

In some embodiments, the dialkyl dithiophosphate is used in an excess relative to the starting material (e.g., piperidine-4-carboxamide 1). The molar amount of dialkyl dithiophosphate may be one of several different values or fall within one of several different ranges. For example, it is within the scope of the present disclosure to select a molar amount of dialkyl dithiophosphate to be one of the following values: about 2.1 equivalents, about 2.2 equivalents, about 2.3 equivalents, about 2.4 equivalents, about 2.5 equivalents, about 2.6 equivalents, about 2.7 equivalents, about 2.8 equivalents, about 2.9 equivalents, about 3.0 equivalents, or more than about 3.0 equivalents relative to the molar amount of carboxamide substrate. It is likewise within the scope of the present disclosure for the molar amount of dialkyl dithiophosphate to fall within one of many different ranges. In a first set of ranges, the range of dialkyl dithiophosphate is one of the following: about 2.0% to about 3.0%, about 2.1 to about 2.9%, about 2.2% to about 2.8%, about 2.3% to about 2.7%, and about 2.4% to about 2.6% relative to the molar amount of carboxamide substrate.

The temperature at which the reaction of the dialkyl dithiophosphate and the starting material (e.g., piperidine-4-carboxamide 1) is conducted may be one of several different values or fall within one of several different ranges. For example, it is within the scope of the present disclosure to select a reaction temperature to be one of the following values: about 60° C., about 65° C., about 70° C., about 75° C., about 80° C., about 85° C., about 90° C., about 95° C., about 100° C., about 105° C., about 110° C., or greater than about 110° C. It is likewise within the scope of the present disclosure for the reaction temperature to fall within one of many different ranges. In a first set of ranges, the temperature is one of the following: about 60° C. to about 125° C., about 65° C. to about 120° C., about 70° C. to about 115° C., about 75° C. to about 115° C., about 80° C. to about 115° C., about 85° C. to about 115° C., about 90° C. to about 115° C., about 95° C. to about 115° C., about 100° C. to about 115° C., and about 105° C. to about 115° C. In some embodiments, at least a portion of the reaction is conducted at the reflux temperature of the solvent. A variety of solvents may be used in accordance with the present teachings. In some embodiments, an organic solvent is used. In some embodiments, the solvent is aromatic. In some embodiments, the solvent is toluene.

The time during which the dialkyl dithiophosphate and the starting material (e.g., piperidine-4-carboxamide 1) are allowed to react may be one of several different values or fall within one of several different ranges. For example, it is within the scope of the present disclosure to select a reaction time to be one of the following values: about 1 hour, about 1.5 hours, about 2.0 hours, about 2.5 hours, about 3.0 hours, about 3.5 hours, about 4.0 hours, about 4.5 hours, about 5.0 hours, about 5.5 hours, about 6.0 hours, about 6.5 hours, about 7.0 hours, about 7.5 hours, about 8.0 hours, or greater than about 8.0 hours. It is likewise within the scope of the present disclosure for the reaction time to fall within one of many different ranges. In a first set of ranges, the reaction time is one of the following ranges: about 1 hour to about 10 hours, about 2.0 hours to about 9.5 hours, about 3.0 hours to about 9.0 hours, about 3.5 hours to about 8.5 hours, about 4.0 hours to about 8.5 hours, about 4.5 hours to about 8.5 hours, about 5.0 hours to about 8.5 hours, about 5.5 hours to about 8.5 hours, about 6.0 hours to about 8.5 hours, about 6.5 hours to about 8.5 hours, and about 7.0 hours to about 7.5 hours.

The ability to directly convert piperidine-4-carboxamide 1 to piperidine-4-thiocarboxamide 2 is surprising and unexpected in view of the conventional wisdom that an intermediate is required to effect this transformation. For example, it has been reported that piperidine-4-carboxamide 1 cannot be directly converted to piperidine-4-thiocarboxamide 2 using conventional thionation reagents such as phosphorus sulfide ($P_4S_{10}$), and that attempting to use such reagents leads instead to the aromatized thioisonicotinamide 6, as shown in EQN. 3.

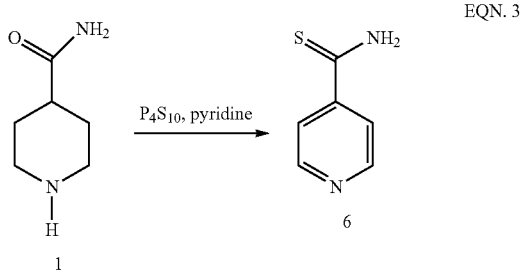 [SMILES: NC(=O)C1CCNCC1 ; NC(=S)c1ccncc1]

EQN. 3

Thus, it is surprising and unexpected that dialkyl dithiophosphates have been found to provide good direct conversion of piperidine-4-carboxamide 1 to piperidine-4-thiocarboxamide 2 although conventional wisdom held that such a direct transformation was not feasible. The success is especially surprising and unexpected in view of the fact that dialkyl dithiophosphates have not previously been used as thionating agents for substrates that contain a piperidine moiety or, for that matter, a secondary amine. It is also surprising and unexpected that the isolation of the piperidine-4-thiocarboxamide 2 product from the phosphate salts at the end of the reaction after quenching with base was relatively easy.

In view of the conventional wisdom that piperidine-4-thiocarboxamide 2 cannot be directly prepared from piperidine-4-carboxamide 1, various indirect routes have been proposed instead. For example, one conventional method for preparing PTCA 2 is outlined in Scheme 2 (*J. Org. Chem.*, 1957, 22, 984). This route involves the intermediacy of 4-cyanopiperidine 5. As shown in Scheme 2, the pre-formed intermediate 4-cyanopiperidine 5 is reacted with hydrogen sulfide in the presence of aqueous ammonia in methanol to form the piperidine-4-thiocarboxamide product 2.

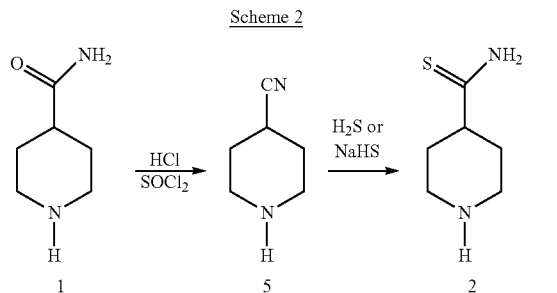

The procedure outlined in Scheme 2 has several deficiencies. First, hydrogen sulfide is a toxic gas and is dangerous to handle. Second, 4-cyanopiperidine 5 is thermally unstable and is subject to auto-accelerating decomposition at only moderately high temperatures. Third, the present inventors found that the yield of 2 as reported in the published procedure is not reproducible, and that appreciable amounts of the 4-cyanopiperidine 5 intermediate are hydrolyzed back to the starting amide 1. Moreover, formation of the 4-cyanopiperidine intermediate 5, which is prepared by reacting piperidine-4-carboxamide 1 with HCl and thionyl chloride, adds another step to the process. It would be economically beneficial not to proceed through a 4-cyanopiperidine 5 intermediate but rather to produce PTCA 2 directly from the amide 1.

Although reported attempts to produce PTCA 2 directly from the amide 1 using phosphorus pentasulfide failed, as described above in reference to EQN. 3, the present inventors found that a high conversion (as determined by $^1H$ and $^{13}C$ NMR) to the desired piperidine-4-thiocarboxamide 2 may be effected—and aromatization of the piperdine ring of amide 1 suppressed—by conducting the reaction between piperidine-4-carboxamide 1 and $P_4S_{10}$ in pyridine at a lower temperature (80° C. vs. 110° C.). Unfortunately, isolation of the thiocarboxamide product 2 from the reaction mixture using normal caustic treatment was unsuccessful.

A second indirect method for preparing PTCA 2 that has been used is outlined in Scheme 3. First, the piperidine ring nitrogen of piperidine-4-carboxamide 1 is protected with a tert-butyloxycarbonyl group (t-BOC) protecting group prior to thionation. The t-BOC protected intermediate 7 is then thiolated using $P_4S_{10}$ or 2,4-bis(4-methoxyphenyl)-1,3,2,4-dithiadiphosphetane-2,4-dithione (Lawesson's Reagent) to form the t-BOC protected thioamide 8. Removal of the t-BOC protecting group furnishes PTCA 2, as shown in Scheme 3.

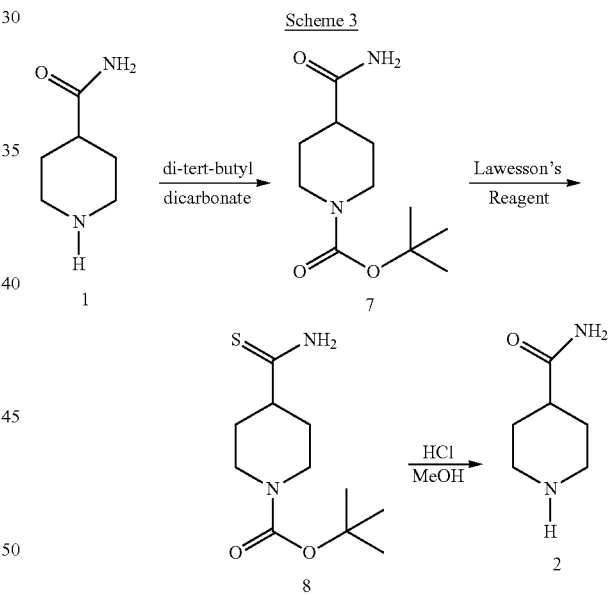

The method shown in Scheme 3 avoids dehydrogenation of the piperdine ring of the carboxamide 1. However, the outlined strategy is costly since (a) the protection-deprotection sequence adds additional steps to the overall process, (b) the protecting group reagents are expensive, and (c) large organic waste streams are produced. In addition, the Lawesson's Reagent used for the thionation of protected intermediate 7 is itself expensive, and also generates large volumes of organic waste.

The following examples and representative procedures illustrate features in accordance with the present teachings, and are provided solely by way of illustration. They are not intended to limit the scope of the appended claims or their equivalents.

EXAMPLES

Example 1: Reaction of Piperidine-4-Carboxamide 1 With O,O'-Diethyl Dithiophosphate To a one-liter flask was charged piperidine-4-carboxamide 1 (0.39 mole) and 500 mL toluene. While stirring the resulting slurry, O,O'-diethyl dithiophosphate (0.99 mole) was slowly added to the flask. During the addition, the flask temperature rose to 110° C. After completion of the addition, the reaction mixture was held under reflux for 7.5 hours and then cooled to ambient temperature. The reaction mixture was a two phase system at this point and a sample of the bottom phase analyzed by $^1$H and $^{13}$C NMR showed the piperidine-4-carboxamide 1 to piperidine-4-carbothioamide 2 conversion was approximately 85-90%. Water (100 mL) was then added to the flask and the flask was warmed to 50° C. to dissolve the bottom phase into the water. The layers were separated and the bottom, aqueous layer was adjusted to pH 13 using 50% NaOH. The slurry that formed was stirred for about 30 minutes and then filtered to recover the solids. The solids were washed with water (50 mL) and dried. The weight of the recovered piperidine-4-carbothioamide 2 represented a 67% yield.

Example 2: Reaction of Piperidine-4-Carboxamide 1 With In Situ Generated O,O'-Diethyl Dithiophosphate To a one-liter flask was charged $P_4S_{10}$ (0.24 mole) and toluene (500 mL). While stirring the resulting slurry, ethanol (1.96 mole) was slowly added to the flask. During the ethanol addition, the flask temperature rose to 45° C. After completion of the ethanol addition, the reaction mixture was slowly heated to reflux during which time the solids dissolved to give a clear solution. The solution was cooled to 70-80° C. and piperidine-4-carboxamide 1 (0.39 mole) was added to the flask in portions while maintaining the temperature at 70-80° C. Once all of the piperidine-4-carboxamide 1 had been added, the reaction mixture was heated to reflux and held for 5-7 hours then cooled to ambient temperature. $^1$H and $^{13}$C analysis showed the conversion of the piperidine-4-carboxamide 1 to piperidine-4-carbothioamide 2 was approximately 85-90%. Water (100 mL) was then added to the flask and the flask was warmed to 50° C., to dissolve the bottom phase into the water. The layers were separated and the bottom, aqueous layer containing the product was adjust to pH 13 using 50% NaOH. The slurry that formed was stirred for about 30 minutes and then filtered to recover the solids. The solids were washed with water (50 mL) and dried. The recovered solids represented a 67% recovered yield of piperidine-4-carbothioamide 2.

Example 3: Reaction of Piperidine-4-Carboxamide 1 With In Situ Generated O,O'-Dibutyl Dithiophosphate The procedure of Example 2 was repeated using 1-butanol in place of the ethanol. Conversion of the piperidine-4-carboxamide 1 to piperidine-4-carbothioamide 2 by 1H NMR was 88%. After pH treatment, filtration, and drying, piperidine-4-carbothioamide 2 was obtained in 94% yield.

Example 4: Reaction of Piperidine-4-Carboxamide 1 With In Situ Generated O,O'-Di-Iso-Propyl Dithiophosphate The procedure of Example 2 was repeated using 2-propanol in place of the ethanol. Conversion of the piperidine-4-carboxamide 1 to piperidine-4-carbothioamide 2 in this run was about 50% by NMR analysis after 6 hours at reflux. After workup, piperidine-4-carbothioamide 2 was obtained in 40% yield.

Example 5: Reaction of Piperidine-4-Carboxamide 1 With In Situ Generated O,O'-Dimethyl Dithiophosphate The procedure of Example 2 was repeated using methanol in place of ethanol. The product mixture became very thick to sample for follow up using NMR. The reaction was quenched with water after 5 hours at reflux, and the aqueous layer was separated and pH adjusted to 12 using 50% NaOH. The precipitated solid was filtered and washed with water to give the crude product, piperidine-4-carbothioamide 2 (15.7 g), in 28% yield.

Example 6: Reaction of Piperidine-4-Carboxamide 1 With In Situ Generated O,O'-Dioctyl Dithiophosphate The procedure of Example 2 was repeated using 1-octanol in place of ethanol. Conversion of the piperidine-4-carboxamide 1 to piperidine-4-carbothioamide 2 by $^1$H NMR was almost quantitative.

Example 7: Reaction of Piperidine-4-Carboxamide 1 With In Situ Generated O,O'-Di-(2-methoxyethyl) Dithiophosphate The procedure of Example 2 was repeated using 2-methoxyethanol in place of ethanol. Conversion of the piperidine-4-carboxamide 1 to piperidine-4-carbothioamide 2 by $^1$H NMR was 85%. After pH treatment, filtration, and drying, piperidine-4-carbothioamide was obtained in 78% yield.

It is to be understood that use of the indefinite articles "a" and "an" in reference to an element (e.g., "a carboxamide," "a heteroatom," etc.) does not exclude the presence, in some embodiments, of a plurality of such elements.

The foregoing detailed description and representative examples have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

What is claimed is:

1. A process for preparing piperidine-4-thiocarboxamide comprising:
    reacting piperidine-4-carboxamide with di-(2-methoxyethyl) dithiophosphate and/or a salt thereof in an aromatic solvent.
2. The process of claim 1, wherein the aromatic solvent is toluene.

3. The process of claim 1, wherein the process further comprises:
  forming the di-(2-methoxyethyl) dithiophosphate by reacting 2-methoxyethanol with $P_4S_{10}$.

4. The process of claim 3, wherein the step of forming is performed in toluene.

5. The process of claim 3, wherein the step of reacting the piperidine 4-carboxamide comprises adding the piperidine-4-carboxamide to the formed di-(2-methoxyethyl) dithiophosphate in the aromatic solvent.

6. The process of claim 1, wherein the step of reacting is performed at a temperature of about 60° C. to about 125° C.

7. The process of claim 6, wherein the step of reacting is performed at a temperature of about 105° C. to about 115° C.

8. The process of claim 1, wherein the step of reacting is performed at the reflux temperature of the aromatic solvent.

9. The process of claim 1, wherein the di-(2-methoxyethyl) dithiophosphate is used in a molar excess relative to the piperidine-4-carboxamide.

10. The process of claim 9, wherein the molar excess is about 2.1 equivalents to about 3 equivalents relative to the piperidine-4-carboxamide.

\* \* \* \* \*